(12) United States Patent
Metz-Stavenhagen

(10) Patent No.: US 6,537,276 B2
(45) Date of Patent: *Mar. 25, 2003

(54) APPARATUS FOR BRACING VERTEBRAE

(75) Inventor: Peter Metz-Stavenhagen, Bad Wildungen (DE)

(73) Assignee: Stryker Trauma GmbH (DE)

( * ) Notice: Subject to any disclaimer, the term of this patent is extended or adjusted under 35 U.S.C. 154(b) by 39 days.

This patent is subject to a terminal disclaimer.

(21) Appl. No.: 09/846,819

(22) Filed: May 1, 2001

(65) Prior Publication Data

US 2001/0020169 A1 Sep. 6, 2001

Related U.S. Application Data

(63) Continuation of application No. 09/495,261, filed on Jan. 31, 2000, now Pat. No. 6,261,287, which is a continuation of application No. 08/839,540, filed on Apr. 14, 1997, now Pat. No. 6,090,110, which is a continuation of application No. 08/384,639, filed on Feb. 6, 1995, now abandoned, which is a continuation of application No. 08/025,196, filed on Mar. 2, 1993, now abandoned.

(51) Int. Cl.$^7$ .............................................. A61B 17/70
(52) U.S. Cl. .......................................... 606/61; 606/72
(58) Field of Search .............................. 606/60, 61, 72, 606/73

(56) References Cited

U.S. PATENT DOCUMENTS

| 4,047,524 A | | 9/1977 | Hall ............................ 128/69 |
| 4,383,438 A | | 5/1983 | Eaton ......................... 73/61.2 |
| 4,805,602 A | * | 2/1989 | Puno et al. .................. 606/61 |
| 4,854,304 A | | 8/1989 | Zielke ......................... 128/69 |
| 4,946,458 A | * | 8/1990 | Harms et al. ................ 606/61 |
| 5,129,388 A | | 7/1992 | Vignaud ....................... 606/61 |
| 5,207,678 A | * | 5/1993 | Harms et al. ................ 606/61 |
| 5,352,224 A | * | 10/1994 | Westermann ................ 606/61 |
| 5,360,421 A | | 11/1994 | Puno et al. |
| 6,261,287 B1 | * | 7/2001 | Metz-Stavenhagen ....... 606/61 |

FOREIGN PATENT DOCUMENTS

| EP | 0443892 B1 | 8/1991 |
| GB | 2131300 | 7/1986 |
| WO | 9101691 | 2/1991 |

OTHER PUBLICATIONS

R.M. Puno et al., Anterior Spinal Fixation—Clinical and Biomechanical Analysis, Feb. 17–20, 1986, p. 379.
R.M. Puno et al., Biomechanical Analysis of Five Techniques of Fixation For the Lumbosacral Junction, Jan. 19–22, 1987, p. 366.
Rolando M. Puno, M.D. et al., Biomechanical Analysis of Transpedicular Rod Systems, Jan. 21–22 1987, pp. 973–980.
David M. Arnold, M.D., et al., Spine Pedicle Fixation of the Lumbar Spine, Jan., 1992, pp. 83–106.

* cited by examiner

Primary Examiner—Kevin Shaver
Assistant Examiner—Michael B. Priddy
(74) Attorney, Agent, or Firm—Lerner, David, Littenberg, Krumholz & Mentlik, LLP

(57) ABSTRACT

An apparatus for bracing a plurality of vertebrae of the human spine has at least two pedicle screws, each having an annular head with an opening therewithin and including a slot therewithin. Each slot extends into the corresponding opening and includes internal threaded portions. A securing screw to be screwed in each slot is provided. A relatively stiff threaded rod is also provided and is to be inserted into the opening in the head of each of the pedicle screws and to be secured by the securing screws. Adjusting nuts are screwed on the rod and at least one cooperates with each head.

33 Claims, 3 Drawing Sheets

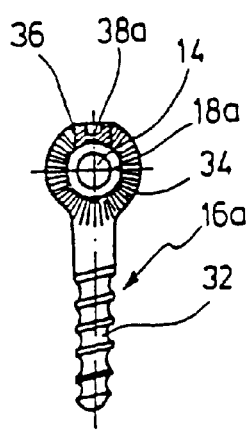
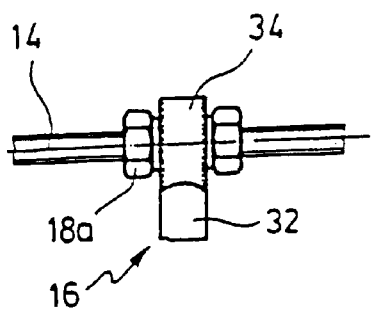
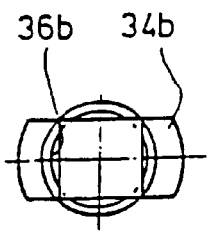
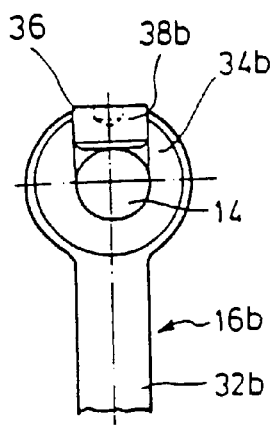
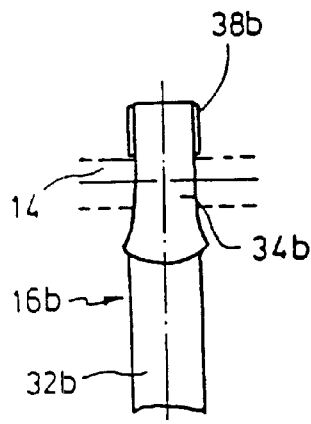
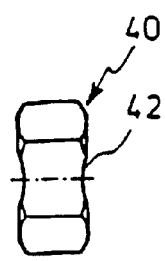
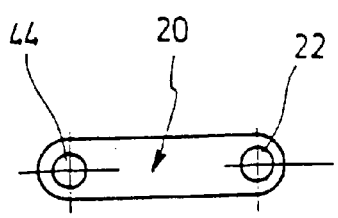
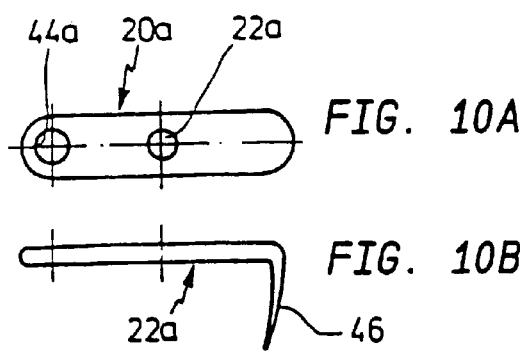

APPARATUS FOR BRACING VERTEBRAE

CROSS-REFERENCE TO RELATED APPLICATIONS

This application is a continuation of U.S. Ser. No. 09/495,261 filed Jan. 31, 2000 now U.S. Pat. No. 6,261,287 which is a continuation of U.S. Ser. No. 08/839,540, filed Apr. 14, 1997, now U.S. Pat. No. 6,090,110 which is a continuation of U.S. Ser. No. 08/384,639, filed Feb. 6, 1995, abandoned which is a continuation of U.S. Ser. No. 08/025,196 filed Mar. 2, 1993, now abandoned.

BACKGROUND OF THE INVENTION

The present invention relates to an apparatus for bracing a plurality of vertebrae of the human spine.

Known supporting means operate with so-called lamina hooks which are disposed on a threaded rod. A compressing means is disclosed in British patent 2 131 300. A distracting means is disclosed in U.S. Pat. No. 4,382,438. The threaded rod bridges a plurality of vertebras and is not suited to act on vertebras which are disposed between the lamina hooks. Before using the supporting means a distraction or, respectively, compression has to be provided by means of an additional device.

German 90 06 646 U1 discloses an apparatus in which a lamina hook is replaced by a clamp-shaped holding member having a pair of legs of which one can be bent with respect to the other. Thereby the giapophysis of the vertebras may be used as anchoring points for the compressing and distracting apparatus.

German 88 02 112 U1 teaches a supporting device for the human spine, according to which the so-called pedicle screws are screwed in the pedicle body of the vertebras. The pedicle screws cooperate with tensioning means which bridge across one or more vertebrae to introduce forces between the vertebrae. The known device affords a primary stabilization of the vertebrae with respect to all degrees of freedom. However, when a number of vertebrae of a non-traumatic spine for example, are to be repositioned, separate means necessary to perform the reposition before the known supporting device may be effectively used.

WO 91/01691 discloses an apparatus for bracing vertebras of the human spine, comprising pedicle screws having slotted heads to receive a rod. The legs of the slotted screw heads include an outer thread on which a nut is screwed which contacts the rod to fix a predetermined position.

EP 0 443 892 discloses a similar device comprising a pedicle screw, the slotted head thereof including internal threaded portions for receiving a fixing screw which is brought into engagement with a serrated or similarly roughened rod to fix the relative position of the rod and the individual pedicle screw. A ring disposed around the head of a pedicle screw is provided so that the legs of the screw head do not spread apart while fixing the rod, as otherwise the engagement between the fixing screw and the screw head may be lost. A similar apparatus is disclosed in WO 90/09156.

Again, the devices last mentioned require separate means for repositioning, thus being suited to maintain a repositioned condition, but not suited to perform repositioning.

It is an object of the present invention to provide an apparatus which is suited to reposition the vertebrae of the human spine as well as to support the vertebrae in the repositioned position thereafter.

The objects are solved by the apparatus of the invention.

SUMMARY OF THE INVENTION

According to the invention, the apparatus uses a threaded rod (i.e., a distracting rod) in combination with lamina hooks. The thread of the rod, however, is not only used to fix the pedicle screws, but further is used to reposition the vertebrae in that an adjusting nut sitting on the threaded rod is turned with respect to the head of the pedicle screw and thus the vertebra has obtained the desired position. By means of the apparatus according to the invention a spine portion is not only distracted or compressed, but individual vertebrae can be effectively repositioned with respect to each other. To this end the threaded rod is designed to be relatively stiff and has a diameter between 7 to 8 mm, for example. On the other hand the rod must be bent to be implanted close to the spine along a bent spine portion. This is facilitated by the design of the pedicle screw heads having slots for receiving the threaded rod. Whereas the screw in the pedicle screw head according to EP 0 443 892, for example, axially fixes the rod, the securing screw of the present invention is merely used to prevent a deflection of the rod out of the receiving slot.

After resetting, the adjusting nut must be fixed on the threaded rod. This can be obtained by means of a suitable counter-nut. Still further, it is possible, to provide the adjusting nut and the front faces of the pedicle screw head with a rotary safety means in form of a toothing or another irregularity cooperating in a clamping fashion. In both cases the nuts are merely fixed by a frictional force. According to a further embodiment of the invention, however, the head of the pedicle screw has a width smaller than the diameter of the securing screw, whereas at least one front face of the adjusting nut has a recess cooperating with the securing screw. Preferably, the adjusting nut includes a plurality of peripherally spaced indentations, wherein the final rotary position of the nut is such that the securing screw cooperates with the indentation. This affords a positive locking of the adjusting nut resulting in a precise rotary locking which cannot be loosened.

The pedicle screws must take up relatively large forces. There is the danger that a pedicle screw breaks out of the bone, primarily when the available bony substance does not provide a sufficiently rigid seat in the vertebra. According to an embodiment of the invention, a mounting strap is attached to the shaft of the pedicle screw laterally extending therefrom, which strap includes an opening for receiving a spongiose screw. The strap has, for example, a pair of openings, wherein one opening receives the shaft of the pedicle screw, while the other opening disposed at the other end of the strap, for example, receives a spongiose screw which is screwed into the vertebra. In this manner, the pedicle screw is laterally stabilized and can receive substantial forces. According to an alternate embodiment of the invention, a mounting strap may be provided to the shaft of the pedicle screw extending therefrom, which strap has a blade or the like to be mounted in the vertebra. The blade is preferably integral with the strap. The blade is beaten into the vertebra wherein the strap may additionally include a hole for receiving a spongiose screw which is screwed into the vertebra. In some cases, a vertebra is displaced with respect to the adjacent vertebra. When the pedicle screw is completely screwed in, it cannot be connected any more with the threaded rod. To accomplish a connection, the pedicle screw is partly screwed into the vertebra bone. According to an embodiment of the invention, the head of the pedicle screw is then rotatably mounted on the screw shaft so that by rotating the shaft the vertebra can be pulled up to the threaded rod for resetting. Preferably the shaft includes tool engaging faces adjacent the head to rotate the shaft of the screw in the desired manner.

In case of very specially displaced individual vertebrae, not even the features referred to above are sufficient. According to a further embodiment of the invention, the upper end of the pedicle screw shaft is ball-shaped, while the pedicle screw head is defined by a ball-engaging cage including a slot for the rod. The cage can be arbitrarily positioned with respect to the shaft of the screw, but can exert a tensioning force to the screw shaft when being screwed in the vertebra. According to both embodiments just referred to, the threaded rod is inserted through a slot of the pedicle screw head, wherein a securing screw referred to several times prevents the rod from sliding out of the slot. Alternatively a closed passage may be provided in the head of the pedicle screw as it is known per se.

Instead of or in addition to the pedicle screw the apparatus of the present invention provides a hook cooperating with a lamina of a vertebra. Those lamina hooks are generally known. According to the invention, however, the lamina hook is provided with a slotted receiving portion to insert the threaded rod. The slot has threaded portions again to secure the rod in the receiving slot.

BRIEF DESCRIPTION OF THE DRAWINGS

Preferred embodiments of the invention will now be described by way of example with reference to the accompanying drawing.

FIG. 3 shows a pedicle screw for the apparatuses according to FIGS. 1 and 2, FIG. 4 shows the pedicle screw of FIG. 3 cooperating with a threaded rod, FIG. 5 schematically shows a side view of a further embodiment of a pedicle screw for the apparatuses of FIGS. 1 and 2, FIG. 6 shows a side view of the pedicle screw of FIG. 5 rotated about 90°, FIG. 7 shows a plain view of the pedicle screw of FIG. 5, FIG. 8 shows a side view of an adjusting nut of the apparatus of FIGS. 1 and 2, FIG. 9 shows a stabilizing strap for the apparatus of FIGS. 1 and 2, FIG. 10 shows a further embodiment of a stabilizing strap of the apparatus of FIGS. 1 and 2.

DETAILED DESCRIPTION OF THE PREFERRED EMBODIMENTS

Figure 1:
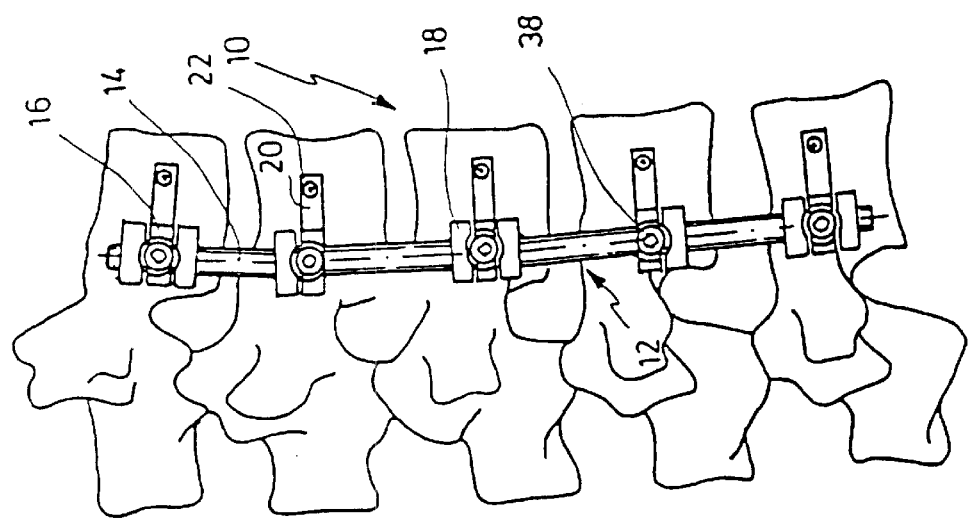
FIG. 1 schematically shows an apparatus according to the invention to be used as a distracting system, FIG. 2 schematically shows an apparatus according to the invention used as a compressing system.

FIG. 1 shows a bent spine portion 10 wherein the individual vertebras shall be distracted by means of a distracting system 12. The system comprises a relatively stiff threaded rod 14 having a diameter of 6 to 9 mm, preferably 7 to 8 mm. It cooperates with an individual pedicle screw 16 screwed in the vertebras. Details of the screws are shown in the following figures. The threaded rod 14 is received in slots of the pedicle screw heads 16 and a plurality of adjusting nuts 18 are disposed on the rod 14, at least one nut each for a pedicle screw 16. Stabilizing latches 20 cooperate with the pedicle screws, which latches include a hole 22 in a distance from the pedicle screw to receive a spongiose screw screwed in the vertebra. By means of the adjusting nut 18 the vertebrae of the portion 10 may be thus adjusted to accomplish a distraction.

Figure 2:
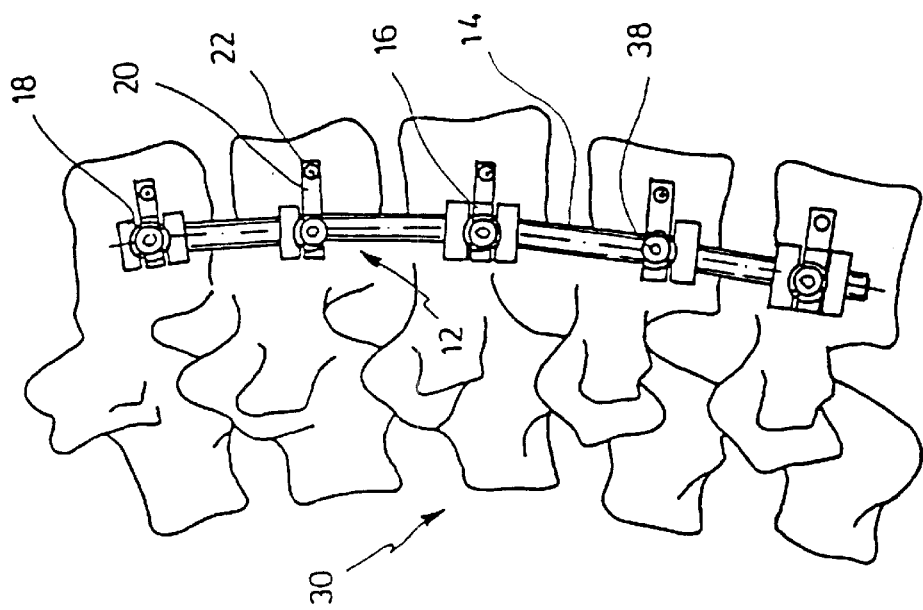

The spine portion 30 shown in FIG. 2 comprises a compressing means including components identical with those shown in the system 12 so that identical components carry identical reference numerals. To reduce the bending of the spine portion 30 a tension force must be exerted on the vertebras to straighten the bent threaded rod 14. This is accomplished by adjusting the individual pedicle screws 16 as described in FIG. 1. In the following the components of the system referred to are described in more detail.

FIG. 3 shows a pedicle screw 16a having a shaft 32 and an annular head 34. The head 34 includes a slot 36 in which the rod 14 is inserted. A securing screw 38a cooperating with threaded portions in the slot 36 holds the threaded rod 14 in the slot 36. FIG. 4 shows adjusting nuts 18a located on either side of the head 34 to displace the screw 16a along the rod 14.

In the embodiment of FIGS. 5 and 6 the pedicle screw 16b has a relatively narrow head 34b so that the securing screw 38b laterally projects. This is shown by the dashed line in FIG. 7. When an adjusting nut 40 according to FIG. 8 is used, which nut is provided with indentations 42 on the opposite front faces thereof, the nut 40 can be secured to the rod 14 when an indentation 42 of the screw 28b cooperates with the adjusting nut 38b.

FIG. 9 shows a mounting strap. The plate-shaped strap 20 includes a first hole 44 receiving the shaft of a pedicle screw. A second hole 22 receives a spongiose screw as mentioned before.

FIG. 10 shows an alternate embodiment 20a of a stabilizing latch, again comprising a hole 44a for a pedicle screw and a hole 22a located substantially in the center for receiving a spongiose screw. FIG. 10 further shows a blade 46 integrally shaped on the end opposite the hole 44a which blade is driven home in the vertebra.

Figure 11:
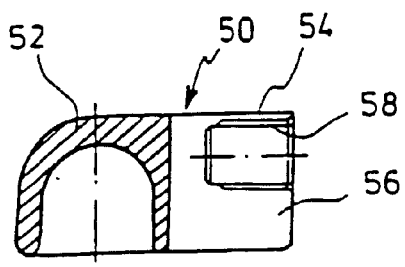
FIG. 11 shows a section of a lamina hook for the apparatus of FIGS. 1 and 2.
Figure 12:
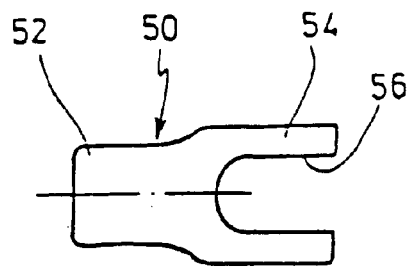
FIG. 12 shows a plain view of the hook of FIG. 11.

FIGS. 11 and 12 show a lamina hook 50 comprising a hook portion 52 and a receiving portion 54 including a slot 56. The slot 56 receives a threaded rod such as the rod 14 shown in FIGS. 1 and 2. Threaded portions as indicated at 58 in FIG. 11 are provided inside the slot 56 to receive a securing screw not shown to hold the rod in the slot 56. The position of the rod in the slot 56 is determined by the position of the securing screw not shown, wherein a relative position between the hook 50 and the rod is possible to a limited extent.

Figure 13:
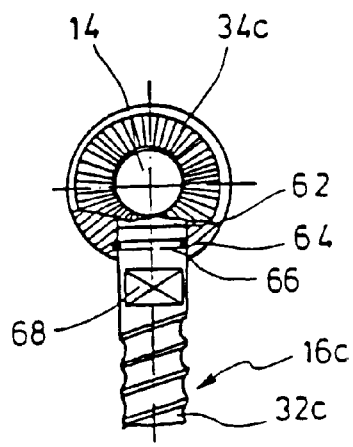
FIG. 13 shows a side view of a further embodiment of a pedicle screw for an apparatus according to the invention.
Figure 14:
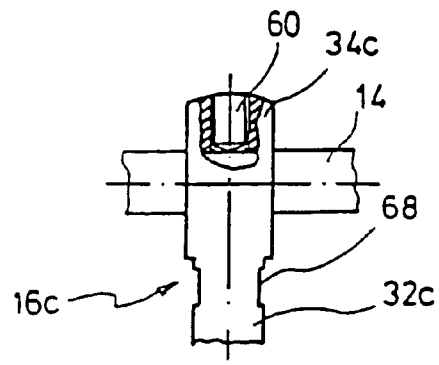
FIG. 14 shows a side view of the pedicle screw of FIG. 13 turned about 90°.

FIGS. 13 and 14 show a pedicle screw 16c comprising a shaft 32c and an annularly closed head 34b through which a rod 14 extends. A fixing screw 60 in the head 34b is used to fix the threaded rod 14. However, adjusting nuts may be used as mentioned before. According to the embodiment of FIGS. 13, 14, the shaft 32c is rotatably mounted in the head 34b. Accordingly, a circular blind bore 62 holds a ring 64 cooperating with an annular groove 66 in the shaft 32. Tool faces 68 facilitate a rotation of the shaft 32c relative to the head 34c when it fixedly sits on the rod 14 for example. It should be understood that the head 34c may provide a slot as shown in FIGS. 3 to 7 for example.

Figure 15:
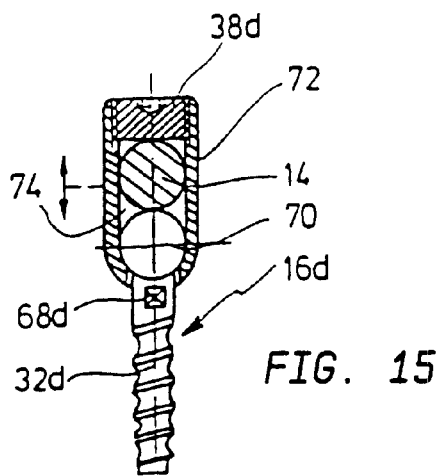
FIG. 15 shows a side view partly in section of a further embodiment of a pedicle screw for an apparatus according to the invention and FIG. 16 shows a side view of the pedicle screw of FIG. 15 turned around 90°.
Figure 16:
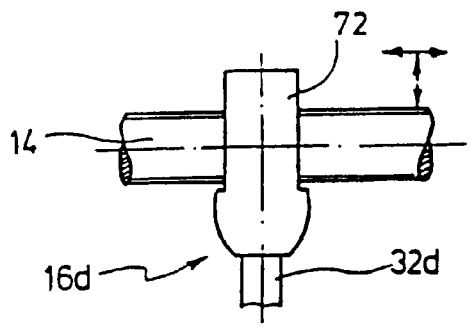

In the embodiment of FIGS. 15 and 16 a pedicle screw 16d is provided comprising a shaft 32d which upper end is formed as a ball 70. A cage 72 cooperates with the ball, the cage further having a passage 74 to receive a threaded rod 14. Furthermore, the cage 72 has threaded portions to receive a securing screw 38d. This allows to rotate the shaft 32, wherein tool faces 68d are provided. Furthermore, the shaft 32d may be pivoted relative to the cage 72 in a limited angle.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A pedicle attachment assembly comprising:
   an anchoring element having a head and a fastening portion to secure said anchoring element to a bone;
   a cage having a longitudinal axis extending between a first end and a second end, a seat for said head, said seat being adjacent said first end, an aperture at said first end and from which said fastening portion extends exterior to said cage when said head is in said seat, a threaded portion adjacent said second end, an opening for receiving a rod such that a rod received therein extends transversely to said longitudinal axis and is positioned above said head, said opening having a surface facing said second end of said cage, whereby a rod arranged in said opening is spaced from said surface; and
   a securing member threadedly engageable with said threaded portion above said rod for axial movement toward said first end.

2. The pedicle attachment assembly in claim 1, wherein said cage may be pivoted with respect to said anchoring element until said securing member generates sufficient locking forces to lock said cage with respect to said head.

3. The pedicle attachment assembly in claim 2 further including a rod disposed in said opening and extending transversely to said longitudinal axis of said cage, and wherein said rod directly engages said head of said anchoring element.

4. The pedicle attachment assembly in claim 1, wherein said fastening portion is threaded.

5. The pedicle attachment assembly in claim 1, wherein said threaded portion of said cage is arranged interiorly on said cage and said securing member is a set screw.

6. The pedicle attachment assembly as set forth in claim 1 further including a rod disposed in said opening and extending transversely to said longitudinal axis of said cage.

7. The pedicle attachment assembly in claim 6, wherein said opening in said cage is in the form of channels open to said second end such that said cage has a U-shaped profile.

8. The pedicle attachment assembly in claim 6, wherein said securing member is a set screw which directly engages said rod and said rod directly engages said head of said anchoring element.

9. The pedicle attachment assembly in claim 1 further including a rod disposed in said opening and extending transversely to said longitudinal axis of said cage, and wherein said head is at least partially spherical, said fastening portion is a threaded portion, and said cage may be pivoted with respect to said anchoring element until said securing member generates a sufficient locking force to lock said cage with respect to said head.

10. The pedicle attachment assembly in claim 9, wherein said opening in said cage is in the form of channels open to said second end such that said cage has a U-shaped profile.

11. The pedicle attachment assembly in claim 9, wherein said seat is at least partially spherical.

12. The pedicle attachment assembly in claim 9, wherein said securing member is a set screw and said threaded portion of said cage is arranged interiorly on said cage.

13. The pedicle attachment assembly in claim 9, wherein said rod directly engages said head of said anchoring element.

14. A pedicle attachment assembly for connecting a pedicle screw to a rod comprising:
   a pedicle screw having a head and a threaded shaft;
   a cage having a hollow inner portion extending along an axis and having an aperture at a first end for surrounding the shaft of said pedicle screw, said cage having a passageway formed adjacent a second end of said cage, opposite said first end and extending transverse to said axis and an axially extending threaded portion adjacent said passageway;
   a rod extending through said passageway transversely to said axis and between said head and said second end; and
   a securing element operatively engaging said threaded portion for axial movement with respect to said axis, wherein a force generated by said element upon axial movement toward said first end of said cage acts through said rod to the head of the pedicle screw.

15. The pedicle attachment assembly as set forth in claim 14 wherein said passageway has a surface facing said second end of said cage, and upon said axial movement of said securing element said rod is spaced from said surface.

16. The pedicle attachment assembly as set forth in claim 14 wherein said pedicle screw shaft includes tool faces for rotating the shaft.

17. The pedicle attachment assembly as set forth in claim 16 wherein said tool faces are on a non-threaded portion of the pedicle screw shaft.

18. The pedicle attachment assembly as set forth in claim 14 wherein said pedicle screw head has at least a partially ball-shaped surface.

19. The pedicle attachment assembly as set forth in claim 18 wherein said cage has an at least partially ball-shaped surface in which said pedicle screw head is seated.

20. The pedicle attachment as set forth in claim 19 wherein said pedicle screw threaded shaft can pivot with respect to said axis of said cage, said pedicle screw head pivoting with respect to said partially ball-shaped surface of said cage.

21. The pedicle attachment assembly as set forth in claim 14 wherein said rod acts directly on said pedicle screw head upon axial movement of said securing element towards said first end of said cage.

22. A pedicle attachment assembly for connecting a pedicle screw to a rod comprising:
   a pedicle screw having a head and a threaded shaft;
   a cage having a hollow inner portion extending along an axis having an aperture at a first end for surrounding the shaft of said pedicle screw;

a passageway extending transverse to said axis formed adjacent a second end of said cage opposite said first end, and an axially extending threaded portion adjacent said second end;

a rod extending through said passageway transversely to said axis; and a threaded securing element operatively engaging said threaded portion for axial movement with respect to said axis, said element generating forces which act on said pedicle screw head through said rod.

23. The pedicle attachment assembly as set forth in claim 22 wherein said passageway has a surface facing said second end of said cage with said rod being spaced toward said second end from said surface.

24. The pedicle attachment assembly as set forth in claim 22 wherein said rod is spaced between said second end and said pedicle screw head.

25. The pedicle attachment assembly as set forth in claim 24 wherein said passageway has a surface facing said second end and said rod is spaced toward said second end from said surface upon axial movement of said securing element.

26. The pedicle attachment assembly as set forth in claim 22 wherein said pedicle screw shaft includes tool faces to rotate the shaft.

27. The pedicle attachment assembly as set forth in claim 26 wherein said tool faces are on a non-threaded portion of the pedicle screw shaft.

28. The pedicle attachment assembly as set forth in claim 22 wherein the pedicle screw head has a ball-shaped surface.

29. The pedicle attachment assembly as set forth in claim 28 wherein the first end of the cage has a ball-shaped surface which cooperates with said ball-shaped surface of said pedicle screw head.

30. The pedicle attachment assembly as set forth in claim 29 wherein said pedicle screw threaded shaft can rotate with respect to said axis of said cage.

31. The pedicle attachment assembly as set forth in claim 30 herein said ball-shaped surface on said pedicle screw head rotates with respect to said ball-shaped surface of the cage.

32. The pedicle attachment assembly as set forth in claim 22 wherein said rod acts directly on said pedicle screw head on movement of said securing element towards said first end of said cage.

33. The pedicle attachment assembly as set forth in claim 22 wherein said threaded portion is located within said hollow inner portion of said cage.

* * * * *

UNITED STATES PATENT AND TRADEMARK OFFICE
CERTIFICATE OF CORRECTION

PATENT NO. : 6,537,276 B2
DATED : March 25, 2003
INVENTOR(S) : Peter Metz-Stavenhagen It is certified that error appears in the above-identified patent and that said Letters Patent is hereby corrected as shown below:

Column 8,
Line 14, "herein" should read -- wherein --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,537,276 B2  
DATED          : March 25, 2003  
INVENTOR(S)    : Peter Metz-Stavenhagen It is certified that error appears in the above-identified patent and that said Letters Patent is hereby corrected as shown below:

<u>Title Page,</u>
After item [63], insert:
-- [30]     Foreign Application Priority Data,
Mar. 2, 1992 (DE) ........................... G 92 02 745.8 --

Signed and Sealed this

Tenth Day of February, 2004

JON W. DUDAS
*Acting Director of the United States Patent and Trademark Office*